(12) United States Patent
Qian (10) Patent No.: US 9,072,735 B2
(45) Date of Patent: Jul. 7, 2015

(54) PROTEINASES DESTROY CANCER TUMOR'S SOLID STRUCTURE AND KILL CANCER CELLS LOCALLY

(76) Inventor: Yong Qian, San Diego, CA (US)

( * ) Notice: Subject to any disclaimer, the term of this patent is extended or adjusted under 35 U.S.C. 154(b) by 433 days.

(21) Appl. No.: 12/900,812

(22) Filed: Oct. 8, 2010

(65) Prior Publication Data
US 2011/0086018 A1    Apr. 14, 2011

Related U.S. Application Data

(63) Continuation-in-part of application No. 11/825,246, filed on Jul. 5, 2007, now abandoned, which is a continuation-in-part of application No. 11/542,442, filed on Oct. 3, 2006, now abandoned.

(60) Provisional application No. 60/723,499, filed on Oct. 3, 2005.

(51) Int. Cl.
*A61K 38/48* (2006.01)
*A61P 35/00* (2006.01)
*C12N 9/50* (2006.01)

(52) U.S. Cl.
CPC .............. *A61K 38/48* (2013.01); *A61K 38/482* (2013.01)

(58) Field of Classification Search
CPC .. A61K 2300/00; A61K 38/48; A61K 38/482
USPC ................. 424/94.63; 435/219; 514/1.1, 13.3
See application file for complete search history.

(56) References Cited

U.S. PATENT DOCUMENTS

2004/0167115 A1 * 8/2004 Dou et al. ................. 514/210.02

FOREIGN PATENT DOCUMENTS

CA    WO/00/04910    2/2000

OTHER PUBLICATIONS

Wald et al. Cancer Chemother Pharmacol. Jul. 2001;47 Suppl:S16-22.*
Williams et al. J. Immunol. Nov. 1, 1994;153(9):4247-55.*
Wilhelm et al. European Journal of Cell Biology 78, 127-133 (Feb. 1999).*
Rutka JT, Apodaca G, Stern R, Rosenblum M. The extracellular matrix of the central and peripheral nervous systems: structure and function. J Neurosurg. Aug. 1988; 69(2):155-70.
Crystal RG. In vivo and ex vivo gene therapy strategies to treat tumors using adenovirus gene transfer vectors. Cancer Chemother Pharmacol. 1999:43 Suppl: S90-9.
N. Kuriyama, H. Kuriyama, C. M. Julin, K. Lamborn, and M. A. Israel. Pretreatment with Protease Is a Useful Experimental Strategy for Enhancing Adenovirus-Mediated Cancer Gene Therapy. Human Gene Therapy. Nov. 2000, 11(16): 2219-2230.
Eikenes L, Bruland ØS, Brekken C, Davies Cde L. Collagenase increases the transcapillary pressure gradient and improves the uptake and distribution of monoclonal antibodies in human osteosarcoma xenografts. Cancer Res. Jul. 15, 2004;64(14):4768-73.
Jones RA, Kotsakis P, Johnson TS, Chau DY, Ali S, Melino G, Griffin M. Matrix changes induced by transglutaminase 2 lead to inhibition of angiogenesis and tumor growth. Cell Death Differ. Sep. 2006;13(9):1442-53. Epub Nov. 18, 2005.
Kuriyama N, Kuriyama H, Julin CM, Lamborn KR, Israel MA. Protease pretreatment increases the efficacy of adenovirus-mediated gene therapy for the treatment of an experimental glioblastoma model. Cancer Res. Mar. 1, 2001;61(5):1805-9.
Netti PA, Berk DA, Swartz MA, Grodzinsky AJ, Jain RK. Role of extracellular matrix assembly in interstitial transport in solid tumors. Cancer Res. May 1, 2000;60(9):2497-503.

* cited by examiner

*Primary Examiner* — Janet Epps-Smith
(74) *Attorney, Agent, or Firm* — Lili Chen (57) ABSTRACT

A proteinase therapy has been invented to eliminate solid tumors by destroying tumors' solid structure and killing cancer cells by cleaving vital extracellular matrix proteins C-terminally, N-terminally or both with cell membrane intact and limited adverse effects. The micro-scale intratumoral proteinase K therapy is tumor specific but not cancer type specific. Proteinase K therapy can be operated on multiple tumors on multiple occasions, if necessary. It may be employed to eliminate any solid tumor to prolong a cancer patient's life span.

8 Claims, 9 Drawing Sheets

PROTEINASES DESTROY CANCER TUMOR'S SOLID STRUCTURE AND KILL CANCER CELLS LOCALLY

CROSS-REFERENCE TO RELATED APPLICATIONS

This application is a continuation-in-part of U.S. application Ser. No. 11/825,246, filed Jul. 5, 2007, now abandoned, which is a continuation-in-part of U.S. application Ser. No. 11/542,442, filed Oct. 3, 2006, now abandoned, which claims the benefit of priority to U.S. provisional application Ser. No. 60/723,499, filed Oct. 3, 2005, each of which is incorporated herein by reference in its entirety.

REFERENCE TO SEQUENCE LISTINGS, A TABLE, OR A COMPUTER PROGRAM LISTING COMPACT DISC APPENDIX

Not Applicable

BACKGROUND OF THE INVENTION

Cancers are collectively a very large group of devastating diseases characterized by uncontrolled cell division, growth, invasiveness and the capability of establishing loci on remote sites (metastasis). Cancer cells also escape from a cancer patient's immune system's screening by expressing self-recognition molecular patterns. Cancer cells invade the immune system when they express immune recognition molecular patterns. Cancer metastasizes through the lymph system, the blood stream and through aggressive local tumor expansion.

Cancers are genetic diseases caused by alterations in cells' genetic material, including changes in DNA sequence, chromosome structure and chromosome number. Different types of cancer are usually caused by different genetic changes, although the same genetic change may occur at different parts of human body. On the other hand, similar types of cancer may have similar genetic changes, except for melanoma, which has the most complicated genetic changes. Cancer cells within a tumor are heterogeneous and have unstable genomes. Due to alternations in chromosome structure and chromosome number, tens to thousands of genes are irregularly expressed. It is not surprising that there is little success in developing anti-cancer drugs that target only one or several gene products or pathways.

When a cancer tumor is found early and is accessible by a surgical knife, surgery is still the most effective and reliable way for a potential cure. Surgery usually cuts extra normal tissue surrounding the tumor, aiming to remove 100% cancer cells in the tumor. However, if the cancer has spread or metastasized, or if the cancer occurs in places a surgical knife cannot access, surgery may not be effective due to technical limitations.

Radiotherapy is another local therapy that kills tumors. However, radiotherapy has enormous side effects which include damaging normal tissues adjacent to the cancer tumor, especially tissues in which cells normally divide rapidly such as those in skin, bone marrow, hair follicles and the lining of the mouth, esophagus, and intestines. Such damages in cells' genetic material may lead to cancer recurrence, new cancer or both. Radiotherapy usually takes about 3 weeks to kill cancer cells in a tumor. However, radiotherapy will not be effective when a cancer tumor is too big or cancer cells have spread.

Other local therapies including cryosurgery and UV local therapy are similar to surgery or radiotherapy, and may be applied to limited parts of the human body.

Intratumoral injection of chemotherapy drugs such as cisplatin is a new method of delivering chemotherapy drugs locally to kill the tumor when its corresponding chemotherapy drug could not kill tumors under the physiologically tolerable dose. However, because chemotherapy drugs are usually small molecules that cannot be confined to the local area, substantial adverse effects, beyond those occurred in systemic chemotherapy, are unavoidable.

Chemotherapy drugs usually target DNA molecules in actively dividing cells in both cancer and normal cells. Thus they do not work against solid-tumors under the safe physiological dose and have side effects which include damage to actively dividing normal cells. Other systemic therapies including immunotherapy, hormonal therapy and gene therapy may be employed to kill cancer cells that have spread. However, just like chemotherapy, these therapies are not effective against solid-tumor cancer cells with different antigens or mutations. Thus, when the metastasis has a few solid-tumors, a combination of systemic and local therapies including surgery, radiotherapy, chemotherapy and immunotherapy are employed according to the cancer type, staging (cancer tumor size, nodal involvement, metastatic progression and pathological classification), and the health status of the patient.

Unfortunately, in many metastases, too many solid-tumors are left for any existing local therapies to handle and, on average, more than 1000 cancer patients die each day in the US alone. There is a great need to find new therapies that can eliminate multiple solid-tumors locally with few side effects.

BRIEF SUMMARY OF THE INVENTION

The foregoing problems are at least partially solved by providing a new local therapy that eliminates multiple tumors for multiple times, if needed, with limited local side effects. The new therapy contains proteinases that cleave the extracellular matrix proteins, including many vital proteins required for cells' survival, and result in cancer cells' death. Proteinase K is one of them. Proteinase K cleaves the extracellular matrix proteins C-terminally on glycine (G or Gly), alanine (A or Ala), valine (V or Val), leucine (L or Leu), isoleucine (I or Ile), phenylalanine (P or Phe), tyrosine (Y or Tyr) and tryptophan (W or Try) amino acid residues and kills cancer cells in vitro and in vivo intratumorally. Intratumoral proteinase K therapy has shown 100% effectiveness on destroying 135 solid tumors in in vivo nude mice models with a safe dosage (about 0.125 to 0.25 mg/tumor about 50-100 $mm^3$). Destroyed tumors originated from human melanoma (CRL-1676 or WM-266-4, 20/20, 100%), human prostate carcinoma (CRL-2505 or 22Rv1, 15/15, 100%), human breast adenocarcinoma (HTB-26 or MDA-MB-231, 18/18, 100%), human breast ductal carcinoma (HTB-129 or MDA-MB-435S, 12/12, 100%), human bronchioalveolar carcinoma (CRL-5807 or NCI-H358, 41/41, 100%), human lung carcinoma (HTB-177 or NCI-H460, 15/15, 100%) and human colon adenocarcinoma (CCL-231 or SW-48, 14/14, 100%). Because of its micro-scale intratumoral delivery system and tumor specificity with limited side effects, proteinase K therapy may be employed to eliminate multiple tumors at multiple sites on multiple occasions to relieve pain caused by tumors' solid structures and more importantly, to increase cancer patients' life spans when it is used alone or properly used with other systemic therapies for metastasized cancer.

Human clinical trials are needed to prove proteinase K's safety and efficacy on human cancer therapy.

These and other objects, advantages, and features of the invention will be better understood by references to the drawings, figures, photos and the detailed description of the invention.

BRIEF DESCRIPTION OF THE SEVERAL VIEWS OF THE DRAWING

For a better understanding of the present invention and to show more clearly how the same may be carried into effect, references will be made, by example, to the accompanying drawings.

DETAILED DESCRIPTION OF THE INVENTION

Cancer is defined as any malignant neoplasm, usually originating from a single cell transformation. By cell type origination, cancers are classified into several types and named accordingly. About 90% of human cancers are carcinomas that arise in the epithelium (layers of cells covering the external surface of the human body and the internal lining of various organs and glands). The other 10% are melanomas, sarcomas, leukemia, lymphomas and gliomas originating from skin pigment cells (melanocytes), supporting tissue of the body (bone, muscle and blood vessels), blood, lymph glands and nerve tissue respectively.

Terms "cancer tissue" and "cancer tumor" refer to cancer at the tissue level. The term "cancer cells" refers to live cancer cells originating from a cancer tissue or tumor at the cellular level. Terms "cancer cell genetic material" or "tumor cancer cell genetic material" refer to DNA and genomes of cancer cells at the molecular level. For a better understanding of cancer, characteristics at different levels of the disease need to be briefly addressed.

At the tissue level, cancer is characterized by uncontrolled growth in tissue or tumor size with irregular shapes. Cancer tissue infiltrates surrounding normal tissue or organs and metastasizes through the lymph system, blood stream and local expansion. Usually, there is a boundary between a tumor and its surrounding normal tissue. This boundary is characterized by the condensed protein network of cancer tumor cells' extracellular matrices full of functional proteins. The well-organized tumor solid structure gives cancer all advantages over the surrounding normal tissue including survival under extreme adverse environments and avoidance of mechanical damages. The internationally known TNM (according to tumor size, nodal involvement and metastatic progression) staging system is widely used clinically to indicate the stage of a cancer progression for each of many cancer diseases including breast cancer, bladder cancer, prostate cancer, cervix cancer, colon and rectum cancer, kidney cancer, lung cancer, melanoma, ovary cancer, stomach cancer, thyroid cancer and uterus cancer. The staging system covers all stages of cancer progression and is used to describe diagnostic results. For example, for breast cancer, T1 stage refers to "the tumor is two centimeters or less in greatest dimension". Unlike the surrounding normal tissue being differentiated and not growing in size in a short term, cancer tissue or tumors are constantly growing and absorb more nutrients from blood vessels around the tumor. When cancer has spread or metastasized, cancer tissue or tumors may be found in many places of a patient's body.

At the cellular level, a cancer tumor is composed of actively dividing cancer cells that often vary in size and are characterized by uncontrolled cell division, growth and capability to spread and to grow new tumors in remote sites. Cancer cells do not follow the normal cell pathway in cell division regulation, growth regulation and differentiation program, and do not undergo apoptosis. Cancer cells in a tumor are networked together as a whole solid structure by their highly expressed functional extracellular matrix proteins. Many of them are vital proteins needed for the growth of the tumor and for the survival of cancer cells. Cancer metastasizes at the cellular level by local tumor expansion and via individual cancer cells migrating off the tumor and spreading through the lymph system and blood stream. A patient's immune system regards cancer cells as "self" and do not attack them.

At the molecular level, a cancer tumor is different from its surrounding tissue or organs in many aspects. First of all, genetic materials in cancer cells are mutated and heterogeneous. These mutations may include, but are not limited to, DNA sequence deletions, duplications, inversions and translocations, and chromosome number changes from diploid to polyploid or aneuploid. Therefore, hundreds to thousands of genes' copy number, regulation and expression patterns are changed, in addition to the expression of oncogenes and the loss or suppression of tumor suppressor genes. In addition to these, the constant mutation nature of cancer cell genomes in a tumor may explain why anti-cancer drugs targeting one to several cancer associated antigens are not working against solid tumors. Even though the gene expression pattern, level, pathway and molecule species in tumor cells are different from those in normal cells due to their genetic differences, cancer cells' expression of self-recognition molecular pattern, including major histocompatibility complex I or MHC I, is not changed and this enables them to escape from a patient's immune screening. Furthermore, when cancer cell mutants express immune recognition molecular patterns, such as MHC II, they begin to infiltrate or invade the lymph system for metastasis. Secondly, the extracellular matrix proteins (ECMPs) of tumor cells form a solid structure or shield on the outside layer of the tumor. This structure may be the barrier, both biochemically and physically, for anti-cancer drugs. The ECMPs are mostly, if not all, functional proteins and many of them are vital proteins that are required for cells' survival. The permanent damage on these proteins C-terminally, N-terminally or both will lead to the death of cancer cells and of actively dividing normal cells as well. Differentiated cells' ECMPs are composed of glycoproteins, lipoproteins, methylated proteins and limited species of particular functional proteins, in addition to structural proteins and self-recognition molecular patterns. Normal cells surrounding a tumor may have few species of vital proteins and may express proteinase resistant ECMPs such as glycoproteins, lipoproteins, and methylated proteins. These enable proteinase K to work against extracellular matrix proteins of tumor cells and kill them specifically with little damage to the surrounding normal cells.

The function of tumor cells is different from that of normal cells. Normal cells undergo a differentiation process and function according to their locations, surrounding environment and compartmentation. After differentiation, normal cells turn into over 200 different cell types and function as specialized cells to serve the needs of various parts of the body. One particularly important function of a normal cell is programmed cell death or apoptosis when needed. Because of the specialized function, normal non-actively dividing cells may not have vital proteins such as the growth factor receptors which actively dividing cells including cancer cells must have. Unlike normal cells, cancer cells do not differentiate and do not have cell cycle, division and growth control, and function as a disease that effectively and selectively takes nutrients to build a bigger solid-structured tumor. Blood vessels are often formed around a tumor to meet the demand of more nutrients for cancer cells' new cell division and growth on the outside surface of the tumor. Extracellular matrix proteins play a key role in selectively absorbing nutrients for a tumor's growth and growth factor receptors signal the division, growth and expansion of individual cancer cells. The elimination or permanent damage of vital proteins such as growth factor receptors and cell skeleton proteins will result in cell death, such permanent arrest, necrosis and/or apoptosis.

In the previous patent application (Ser. No. 11/542,442 on Oct. 3, 2006), bioknives were proposed for cytoreductive therapy on cancer tumors. When testing the concept in experiments, several surprising discoveries were made. First of all, some proteinases, including pronase and proteinase K, were able to separate confluent cancer cells into individual cells more quickly and more completely than trypsin does. Secondly, these proteinases were able to kill cancer cells in vitro while keeping cell membrane intact. Thirdly, proteinase K separated cancer cells were not able to grow tumor on nude mice, although the same number of cells was used with the same procedures as those used when using trypsin. Finally, proteinase K alone was not only able to destroy cancer tumor's solid structure but also able to kill separated cancer cells while keeping cell membrane intact. The dead cells are under arrest, necrosis or apoptosis.

Human cancer cell lines including those from human melanoma (CRL-1676 or WM-266-4), human prostate carcinoma (CRL-2505 or 22Rv1), human breast adenocarcinoma (HTB-26 or MDA-MB-231), human breast ductal carcinoma (HTB-129 or MDA-MB-435S), human bronchioalveolar carcinoma (CRL-5807 or NCI-H358), human lung carcinoma (HTB-177 or NCI-H460) and human colon adenocarcinoma (CCL-231 or SW-48) were purchased from American Type Culture Collection (ATCC, Manassas, Va.). Cancer cell lines were grown in RPMI-1640 Medium (ATCC, Manassas, Va.) supplemented with 5% fetal bovine serum (FBS, ATCC, Manassas, Va.) in tissue culture flasks of 25 cm$^2$ (Becton Dickinson Labware, Franklin Lakes, N.J.), 75 cm$^2$ (Greiner Bio-One GmbH, Frickenhausen, Germany) flasks and 24-well plates (Corning Incorporated, Corning, N.Y.) inside an Infrared $CO_2$ Incubator (Form a Scientific, Waltham, Mass.) with 5% $CO_2$ and 98% humidity at 37° C. Cancer cell lines were also grown in Leibovitz's L-15 medium (ATCC, Manassas, Va.) with 5% FBS inside an incubator (VWR Scientific, West Chester, Pa.) with free air exchange and 98% humidity at 37° C. When cells were confluent, or covered more than 90% area of the tissue culture flask, as seen under an inverted microscope (PhotoZoom, Cambridge Instruments, Cambridge, Mass.), the flask was moved to a Biosafety Cabinet (NuAire Corp., Plymouth, Minn.) with a sterile inside environment. All procedures including medium changes, treatments of cells with various buffers, solvents or proteinases were under sterile conditions.

Sterile and distilled water was used to prepare various reagents or to reconstitute enzymes. Sterile pipette tips of 20 μL, 200 μL and 1000 μL aided with pipetmans and sterile pipettes of 2 mL, 10 mL, 25 mL and 50 mL with a vacuum Pipet-Aid (Broomall, Pa.) were used to transfer sterile agents in the Biosafety Cabinet. Cancer cells were separated by trypsin or other proteinases, or the combination of several proteinases under conditions optimal for enzyme action. The degree of cell separation was viewed under the inverted microscope. Porcine trypsin (0.25%) in Hanks' Balanced Salt Solution without $MgSO_4$ and Tryple™Express, a trypsin replacement, was purchased from Invitrogen in Carlsbad, Calif. Accutase™, Accumax™ and lab chemicals were purchased from Sigma-Aldrich, St. Louis, Mo. Other proteinases, including carboxypeptidase B, elastase grade II lyophlizate, papain, pepsin from porcine stomach, human plasmin, pronase, proteinase K, endoproteinase Glu-C, endoproteinase Asp-N, endoproteinase Lys-C, endoproteinase Arg-C, chymotrypsin and carboxypeptidase Y were purchased from Roche Diagnostics Corp. (Indianapolis, Ind.), Pierce Biotechnology, Inc. (Rockford, Ill.) and GE Healthcare (Piscataway, N.J.), and used for cell separation screenings.

Figure 1:
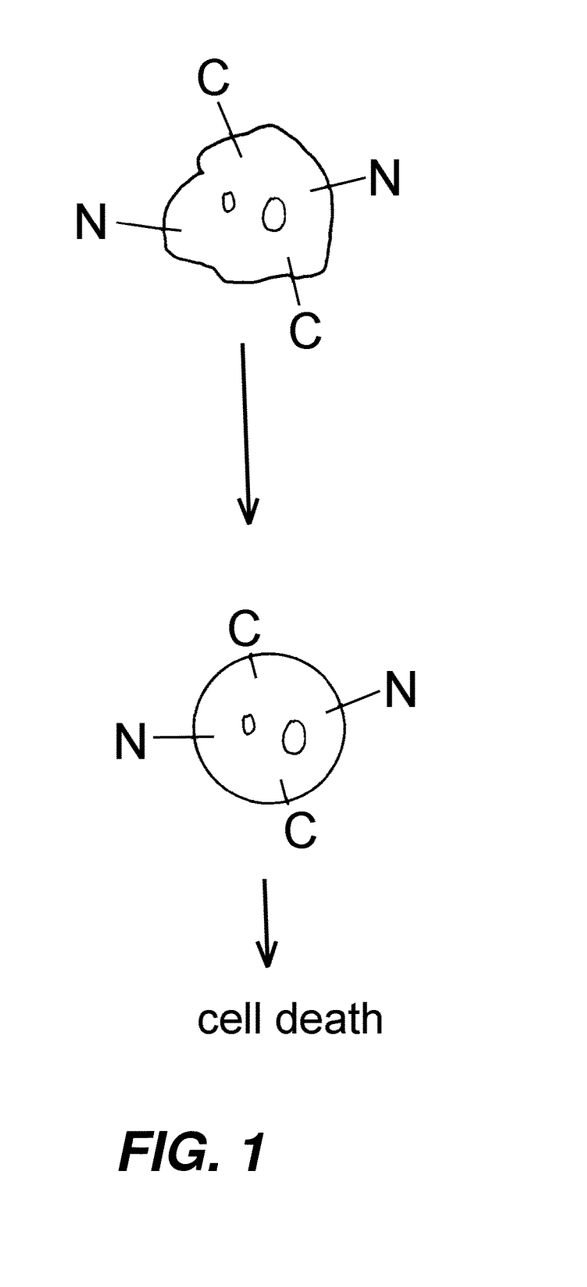
FIG. 1 is a schematic illustration of using proteinases to destroy the solid-structure of a tumor C-terminally and kill cancer cells.

Tumor cells separated and killed by proteinases can be summarized in three groups. FIG. 1 is a schematic illustration of using proteinases to destroy the solid-structure of a tumor C-terminally on ECMPs and to kill cancer cells. One or several proteinases can be applied to cleave cancer cells' ECMPs C-terminally while keeping the cell membrane intact. When extracellular parts of vital proteins including growth factor receptors and cell skeleton proteins are destroyed permanently, cell arrest, necrosis and/or apoptosis occur. After all transmembrane proteins' extracellular C-terminals are cleaved, a tumor's solid structure is destroyed and cells become round in shape. These cancer cells are no longer viable and they are "foreign" because there is no intact self recognition molecule pattern left. If C-terminals of the ECMPs are partially cleaved as in the example of the digestion of trypsin, cancer cells may be able to survive. It is important to keep the cell membrane intact so that the surrounding normal cells' membrane will not be broken and a tumor is eliminated with few side effects.

Figure 2:
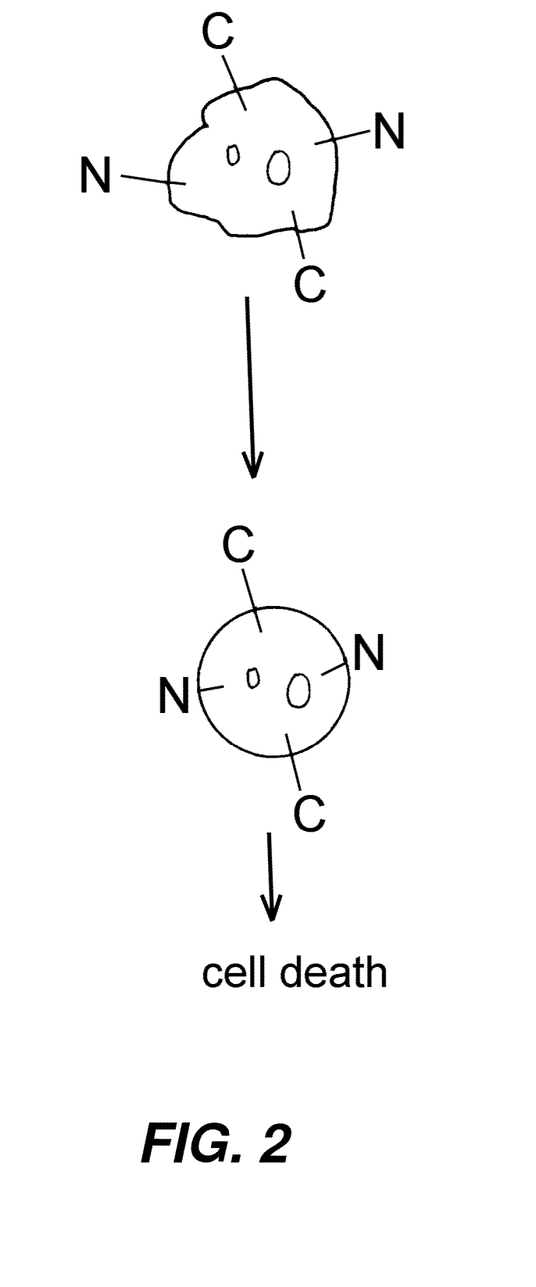
FIG. 2 is a schematic illustration of using proteinases to destroy the solid-structure of a tumor N-terminally and kill cancer cells.

FIG. 2 is a schematic illustration of using proteinases to destroy the solid-structure of a tumor N-terminally on ECMPs and to kill cancer cells. One or several different proteinases can be applied to cleave the ECMPs N-terminally while keeping the cell membrane intact. When extracellular parts of vital proteins are destroyed permanently, cell arrest, necrosis and/or apoptosis occur. After the tumor's solid structure is destroyed, cancer cells become round in shape and are no longer viable. These cells will be attacked by a patient's immune system because of damaged self recognition molecular patterns such as MHC I. Note that all transmembrane proteins' extracellular N-terminals were trimmed up to the surface of the cell membrane. If the damage is partial, such as the example by the digestion of endoproteinase Asp-N, cancer cells may be able to survive. It is important to keep the cell membrane intact so that the surrounding normal cells' membrane will not be broken and a tumor is eliminated with few side effects.

Figure 3:
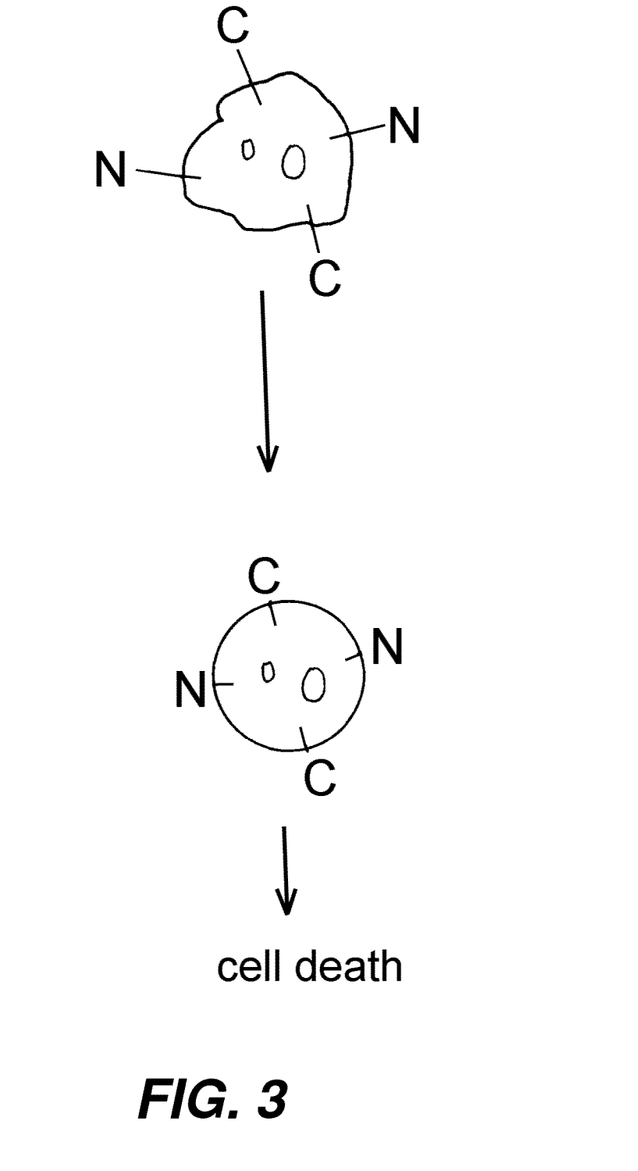
FIG. 3 is a schematic illustration of using proteinases to destroy the solid-structure of a tumor N-terminally and C-terminally, and to kill cancer cells.

FIG. 3 is a schematic illustration of using proteinases to destroy the solid-structure of a tumor N-terminally and C-terminally on the ECMPs and to kill cancer cells. When the ECMPs are trimmed to the surface of the cell membrane, all transmembrane proteins including many vital proteins are damaged and cells get the death signal and have no alternative pathways to survive. These cells are also targets of immune responses because there is no self recognition molecule pattern left anymore. Note that all transmembrane proteins' extracellular C-terminals and N-terminals were cleaved. The majority, if not all, of the vital proteins are permanently damaged which results in cancer cells' death. It is important to keep the cell membrane intact so that the surrounding normal cells' membrane will not be broken and tumors are eliminated with few side effects.

When tumor lines were prepared for tumor growth in nude mice, confluent cells were separated by trypsin or other proteinases and neutralized with fetal bovine serum (FBS) and centrifuged in a culture medium with 10% FBS at 125×g for 8 min. Cell pellet was suspended in phosphate buffer saline (PBS) and centrifuged at 125×g for 8 min. This step was repeated to wash cells one additional time and then the cells were put in an ice bucket with a small amount of PBS. Total cell numbers were calculated using a serial dilution method and the stock suspension was diluted with PBS to a suspension that contained $10^7$ cells/mL. Prepared cell suspension was placed in an ice bucket for 1 hour before being used for nude mice sub-Q injection.

One hundred twenty athymic nude mice (3-4 weeks old, NCR nu/nu, 60 males and 60 females) were purchased from Simonsen Labs (Gilroy, Calif.) and directly delivered to a sterile facility at Molecular Diagnostics Services (San Diego, Calif.). Forty male nude mice were injected with a human prostate tumor line CRL-2505 or 22Rv1 ($1\times10^6$ cells in 100 µL phosphate buffer saline or PBS per animal) subcutaneously with a syringe and a needle sized at 27 gauge. Similarly, 40 female nude mice were injected with a human breast adenocarcinoma tumor line HTB-26 or MDA-MB-231 ($1\times10^6$ cells in 100 µL PBS per animal), and 20 males and 20 females with a human lung carcinoma tumor line HTB-177 or NCI-H460 ($1\times10^6$ cells in 100 µL PBS per animal) subcutaneously.

Very surprisingly, none of the 120 inoculated mice grew any tumors. Furthermore, when subcultured, three cell lines were completely killed due to the treatment with proteinase K. Nevertheless, trypsin treated tumor lines were able to grow tumors in nude mice subcutaneously in a similar procedure. 46 out of 60 nude mice grew tumors from human bronchioalveolar carcinoma tumor line (CRL-5807 or NCI-H358), 17 out of 20 from human lung carcinoma tumor line (HTB-177 or NCI-H460), 14 out of 20 from breast ductal carcinoma tumor line (HTB-129 or MDA-MB-435S) and 14 out of 20 human colon adenocarcinoma tumor line (CCL-231 or SW-48).

Solid-tumors about 50-100 mm³ in volume were treated intratumorally by proteinase K in seven pilot studies ranging from 0.05 to 0.5 mg protein/tumor. The low concentration shows partial effect and the highest concentration had adverse effects. 0.125 to 0.25 mg proteinase K was effective in eliminating solid-tumors 41 out of 41 times (100%) from human bronchioalveolar carcinoma tumor line (CRL-5807 or NCI-H358), 15 out of 15 times (100%) from human lung carcinoma tumor line (HTB-177 or NCI-H460), 5 out of 5 times (100%) from breast ductal carcinoma tumor line (HTB-129 or MDA-MB-435S) and 14 out of 14 times (100%) from human colon adenocarcinoma tumor line (CCL-231 or SW-48). However, adverse effects including bleeding were apparent and cancer cells were not 100% killed over 90% of the time. Further development based on proteinase K's efficacy and reduced adverse effect resulted in the embodiment of the invention utilizing 0.125 mg proteinase K with increased injection volume. This embodiment eliminates tumors and kills cancer cells more completely with fewer adverse effects.

Eighty athymic nude mice (3-4 weeks old, NCR nu/nu, 40 males and 40 females) were purchased from Simonsen Labs and directly delivered to a sterile facility at Anti-cancer, Inc. (San Diego, Calif.).

Melanoma tumors were grown in 14 out of 20 male nude mice and 13 out of 20 female nude mice that were injected with a human melanoma cancer cell line (CRL-1676 or WM-266-4). Great variations in tumor initiation, tumor growth rate, tumor shape and tumor structure were observed. Including seven used for controls, each animal was treated as a "patient" with its own profile, including tumor volume and photos. Tumors were eliminated 100% on 20 tumors when 50-100 uL proteinase K in a concentration of 2.5 mg/mL were administered intratumorally for tumors ranging from 50-100 mm³ in size for the first time. Four animals (20%) were cured. Eight animals (40%) were cured through multiple sequential intratumoral proteinase K therapies. The other eight animals (40%) were treated multiple times but tumor growth recurred. Continuous intratumoral administration of 0.01 to 0.25 mg proteinase K (according to tumor size) was able to control the growth of tumor cancer cells and helped nude mice "patients" live up to their regular life span.

Figure 4A:
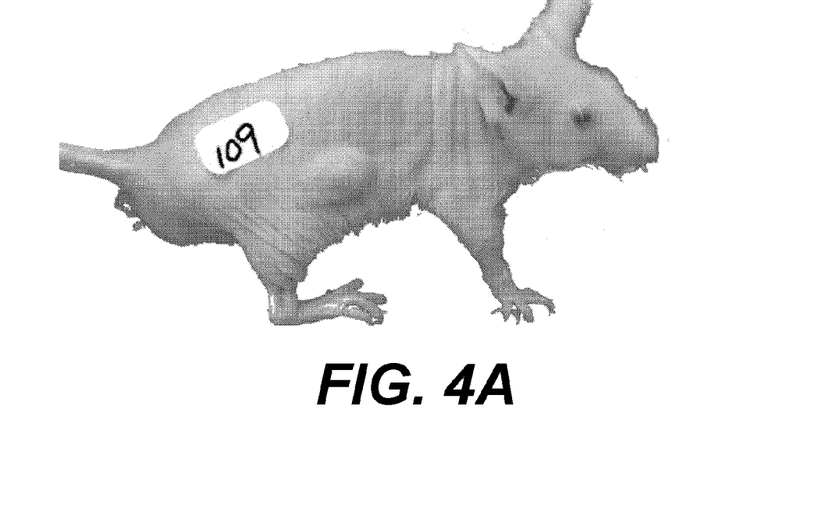
FIGS. 4A, 4B, 5A, and 5B form a set of photos showing proteinase K's action in vivo which has destroyed the solid structure of a human melanoma solid-tumor and killed all cancer cells in nude mouse 109.
Figure 4B:
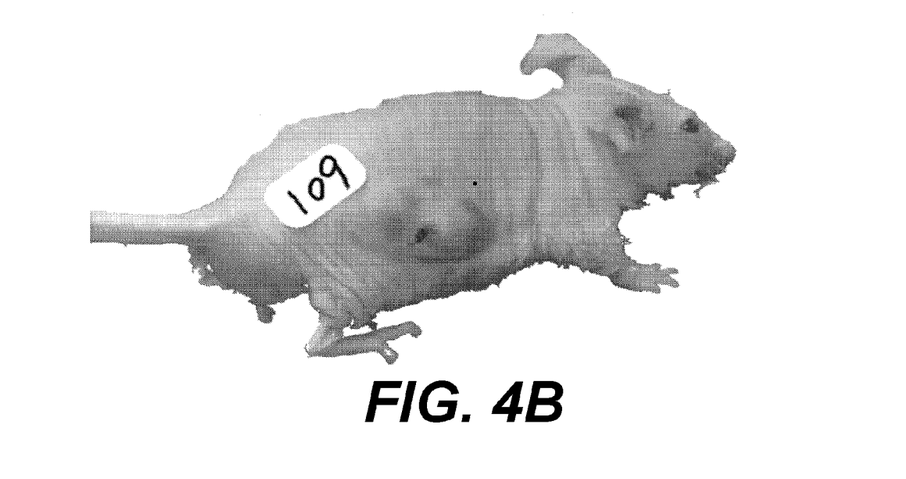

FIGS. 4A, 4B, 5A and 5B show proteinase K intratumoral cure for a solid-tumor, which originated from human melanoma, in nude mouse 109. Nude mouse 109 is a typical example of an animal bearing a tumor treated intratumorally with 0.125 mg proteinase K once and being totally healed without re-treatment (FIG. 4). FIG. 4A shows male nude mouse 109 with one melanoma tumor (CRL-1676 or WM-266-4), with the photo taken before proteinase K intratumoral injection. FIG. 4B shows the same nude mouse 109 with 0.125 mg proteinase K intratumoral injection (50 µL) for two hours. Note that: 1) the color of the tumor changed, 2) the solid-structure of the tumor disappeared and 3) proteinase K's action was restricted mostly to the tumor and a little action on the actively dividing normal cells.

Figure 5A:
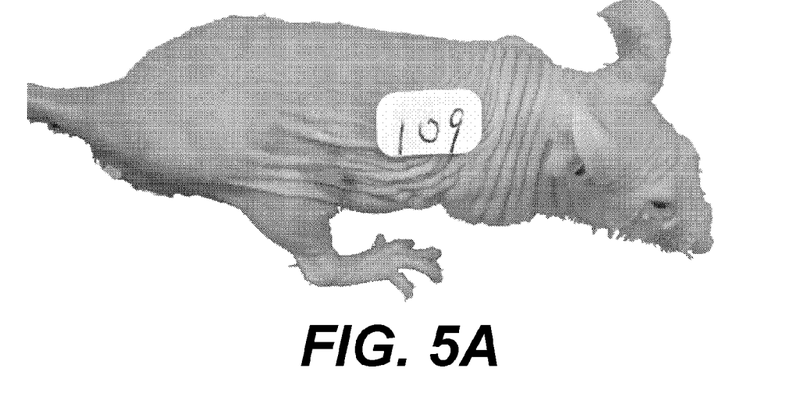
Figure 5B:
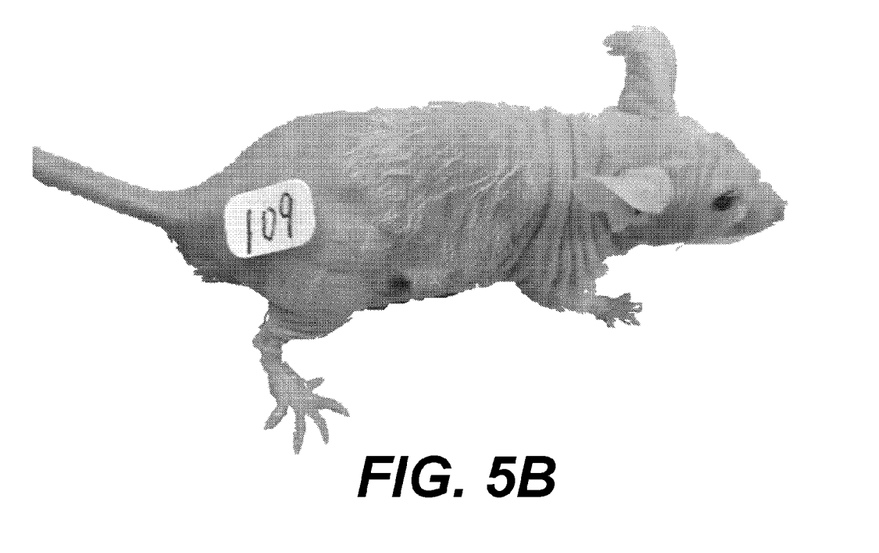

FIG. 5A shows the same nude mouse 109 with one melanoma tumor eliminated by proteinase K for 35 days without recurrence. FIG. 5B shows the same nude mouse 109 with one melanoma tumor eliminated by proteinase K for 49 days without recurrence. The scar area was used for histopathological evaluation.

Histopathological evaluation on the proteinase-treated site indicated that the replicate sections of skin from animal 109 contained a subcutaneous lymph node. The dermis contained a sparse mononuclear cell infiltrate and had no significant histopathologic lesions. An autopsy of the body did not result in any tumors found in the rest of the body.

The second set of proteinase K therapy experiments was on the elimination of solid-tumors originating from human prostate carcinoma cell line (CRL-2505 or 22Rv1) in a nude mice model. Of the fifteen male nude mice with tumors being treated intratumorally with proteinase K, 100% of the tumors were eliminated the first time. Three animals (20%) were cured and cancer cell free. Six animals (40%) had tumors recur and were cured by further intratumoral injection of proteinase K. The other six animals (40%) had multiple proteinase K treatments but were not totally cured. Nevertheless, these animals' tumor growth was brought under control by 0.01 to 0.25 mg proteinase K.

Male nude mouse 135 is an example of a two-tumor bearing mouse being treated several times with proteinase K intratumorally (FIG. 5). FIGS. 6A, 6B, 7A, and 7B show proteinase K (0.125 mg) against solid-tumors originated from human prostate carcinoma cell line CRL-2505 or 22Rv1 in nude mouse 135. Efficacy and safety could be observed. Proteinase K was tumor specific and did little damage to normal cells surrounding the tumor. The scar may be eliminated provided that the waste of killed or eliminated tumor liquid is absorbed by cotton in human clinical applications.

Figure 6A:
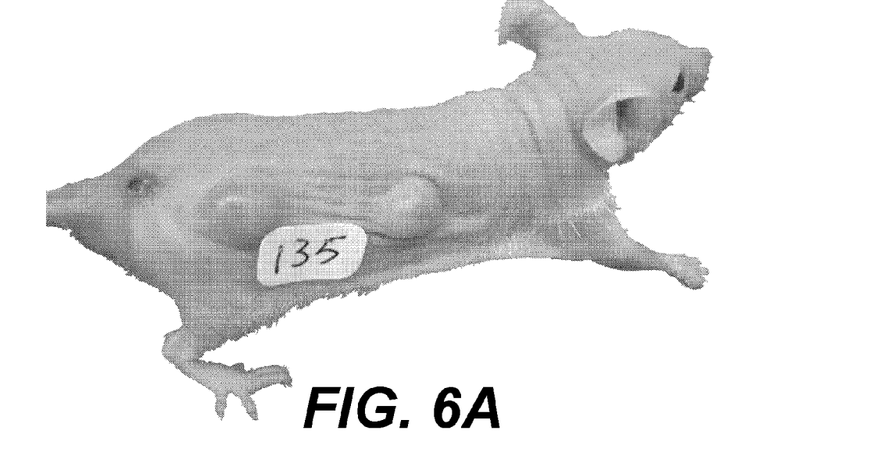
FIGS. 6A, 6B, 7A, and 7B form a set of photos showing proteinase K's action in vivo destroying solid structures of two prostate carcinoma solid-tumors and killing their cancer cells in nude mouse 135.

FIG. 6A shows nude mouse 135 with two prostate tumors (front 113 mm$^3$, rear 98 mm$^3$): the picture was taken before proteinase K treatment for the front tumor. The mouse was labeled between the rear tumor and the base of the tail.

Figure 6B:
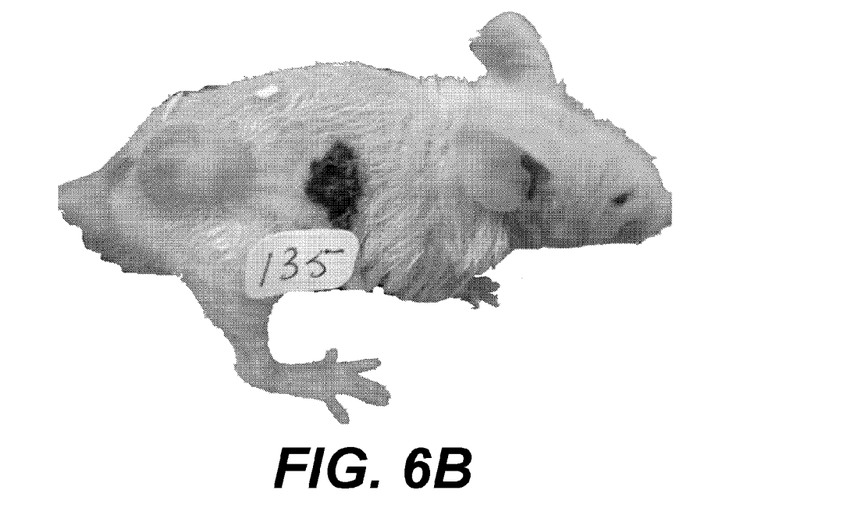

FIG. 6B shows the same 135 nude mouse 4 days older than the mouse in FIG. 6A. Note that 1) the front tumor was eliminated by 0.125 mg proteinase K, 2) the untreated rear tumor grew to 254 mm$^3$ in volume and 3) the mouse grew many hairs.

Figure 7A:
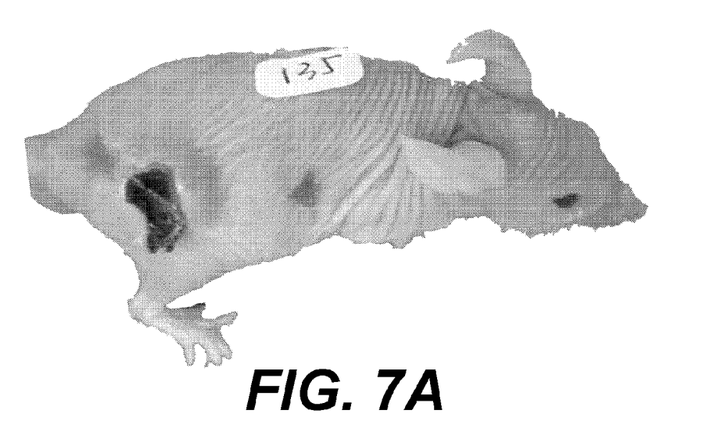

FIG. 7A shows the same nude mouse 11 days older than the mouse in FIG. 6A. Note that 1) the front tumor was eliminated for 11 days, 2) the rear large tumor was treated for a week using the same amount of proteinase K (0.125 mg active) and 3) a third proteinase K (0.075 mg active form of proteinase K) treatment was initiated against the third tumor (94 mm$^3$) located near the rear tumor treated site.

Figure 7B:
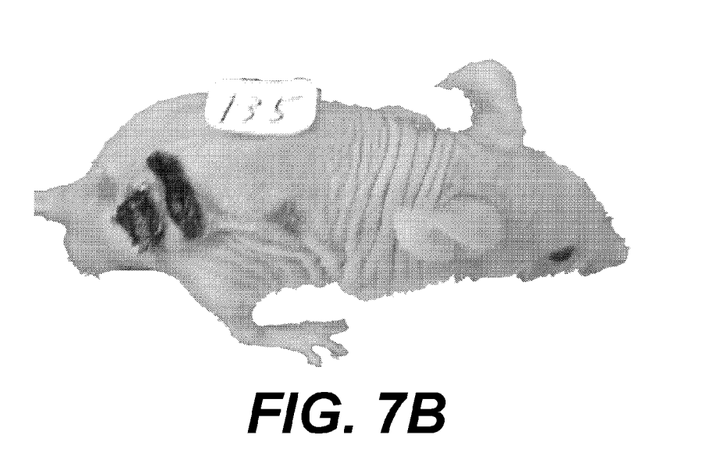

FIG. 7B shows the same nude mouse 14 days older than the mouse in FIG. 6A. Note that 1) the front tumor was eliminated by proteinase K for 14 days, 2) the rear tumor was treated for 10 days and 3) the third tumor was treated by proteinase K for 3 days.

Human breast adenocarcinoma tumors were grown in 16 out of 20 female nude mice injected with cancer cell line HTB-26 or MDA-MB-231. Proteinase K was administered intratumorally to 15 of them and all tumors were eliminated the first time. Of the 15, 6 animals (40%) were cured and 60% had multiple treatments but were not cured although the cancer growth is under the control of 0.01 to 0.25 mg proteinase K.

Figure 8A:
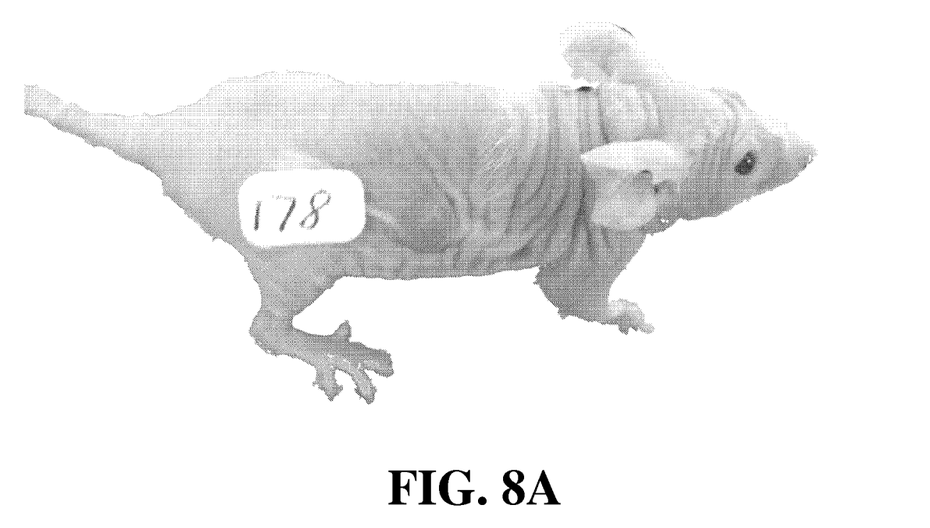
FIGS. 8A, 8B, 9A, and 9B form a set of photos showing proteinase K's action in vivo that destroyed the solid structure of a breast adenocarcinoma solid-tumor and killed its cancer cells in nude mouse 178 and 179.
Figure 8B:
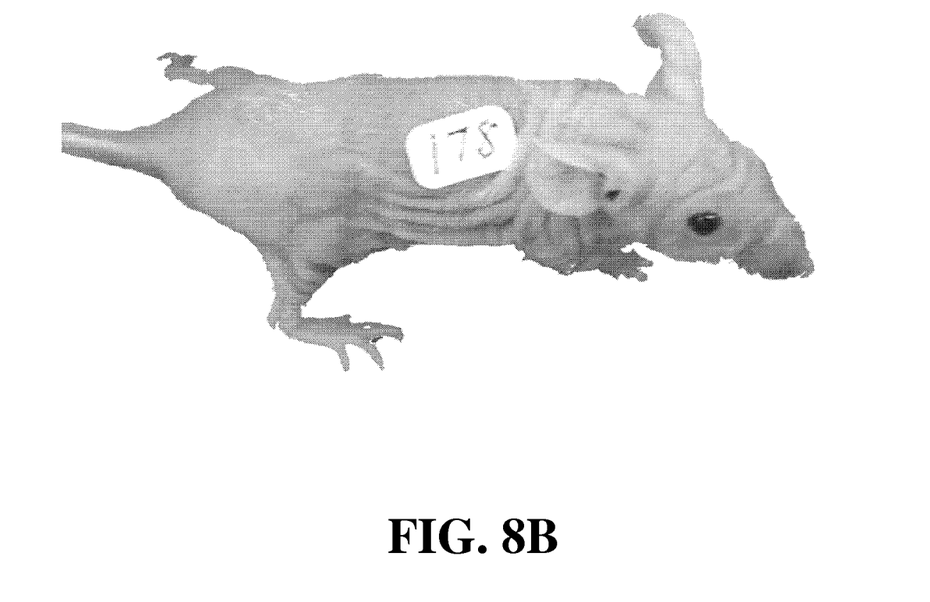
Figure 9A:
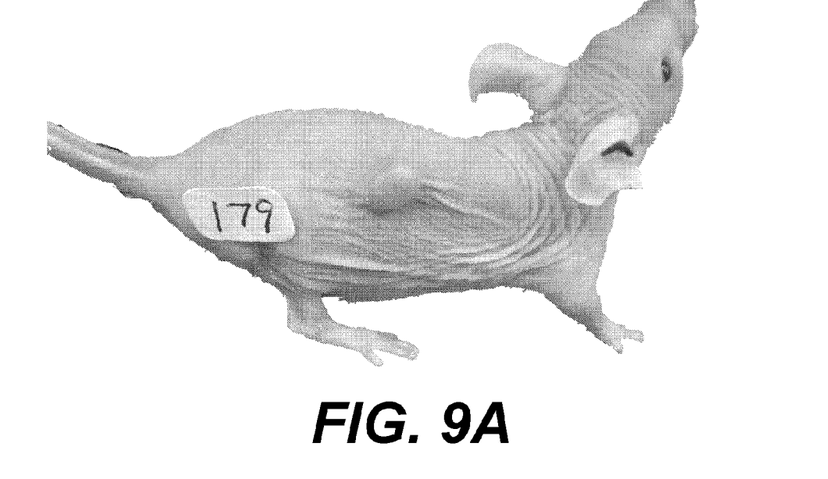
Figure 9B:
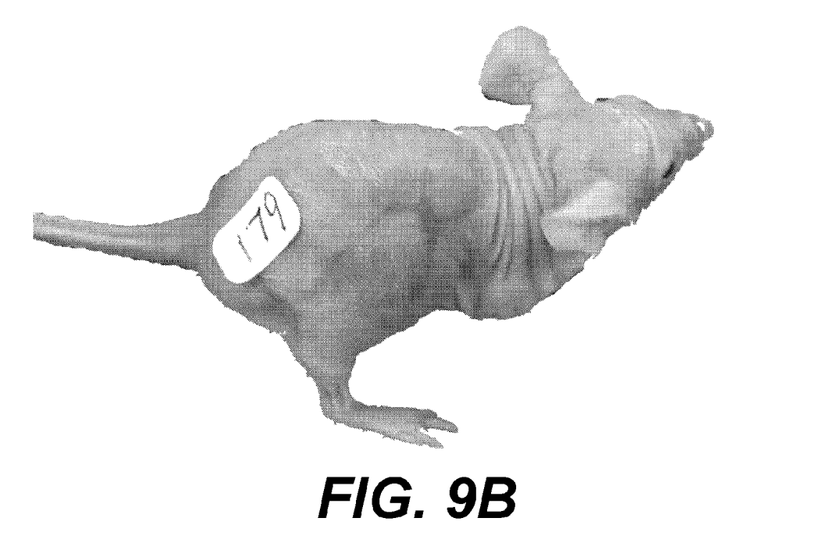

FIGS. 8A, 8B, 9A, and 9B show an example of proteinase K destroying the solid structure of two breast adenocarcinoma tumors intratumorally and killing cancer cells in nude mice 178 and 179. The tumor originated from the human breast adenocarcinoma cell line MDA-MB-231. These mice were tumor free and cancer cell free after 0.125 mg proteinase K therapy. FIG. 8A shows a female nude mouse 178 with one breast adenocarcinoma tumor, with the picture taken before proteinase K treatment. FIG. 8B shows the same nude mouse 178 with intratumoral proteinase K (0.125 mg active proteinase K) injection 22 days post treatment. FIG. 9A shows a female nude mouse 179 with one breast adenocarcinoma tumor, with the picture taken before proteinase K treatment. FIG. 9B shows the same nude mouse 179 with intratumoral proteinase K (0.125-mg active proteinase K) injection 43 days after treatment.

In summary, proteinase K therapy is tumor specific but not cancer type specific. This could be explained by the broad mechanism of action on damaging all vital protein molecules that are located on, in or cross cell membranes, in addition to up to 3,000 species of other functional membrane proteins. After all extracellular and cell membrane proteins are cleaved by proteinase K, the cancer cell is exhausted and under arrest in round shape as seen under microscope. The cell arrest may last up to a month. Other forms of cell death may be necrosis and apoptosis.

Compared to conventional surgery, proteinase K therapy has many advantages: (a) it can eliminate solid-tumors effectively while preserving normal tissue or organ surrounding the tumor; (b) it can operate at any tissue or organ of the body where solid-tumors are located, including places where a surgical knife cannot access; (c) it can operate at multiple places on multiple occasions; (d) the patient may not need to stay in the hospital after the operation; (e) the patient may not experience as great an amount of pain as in conventional surgery and (f) the loss of blood, stress or down regulated immunity may not occur, otherwise suffered after conventional surgery. However, when proteinase K is used to eliminate large tumors from large animals and human beings, much larger amount (0.01 to 1000 mg) of proteinase K, according tumor size, location, inhibitor neutralization and the frequency of use, may be applied.

Because of its micro-scale, proteinase K therapy may be comparable to radiotherapy. However, it has many advantages over radiotherapy: (a) the tumor surrounding normal cells, especially active dividing cells such as those in skin, bone marrow, hair follicles and the lining of the mouth, esophagus, and intestines, will not be damaged genetically; (b) the recurrence of the cancer or the occurrence of new cancer may be greatly reduced; (d) patients may not have radiotherapy related side effects, including the pain and loss of hair; (e) the therapy is shorten by 3 weeks.

Because of its mechanism of action on the extracellular vital proteins, proteinase K has advantages over many chemotherapy drugs that target on DNA. First of all, proteinase K does not cause DNA mutation and its killing of cancer cells is restricted to a tumor, and avoids normal actively dividing cells due to proteinase K's size, pharmacodynamics, pharmacokinetics and distribution. The new therapy may be useful in eliminating all solid-tumors including the seven types which have been tested in the nude mice model so far. It may also be useful in eliminating solid tumors in diseases including adrenocortical carcinoma, appendix cancer, basal cell carcinoma, bile duct cancer, bladder cancer, bone cancer, osteosarcoma/malignant fibrous histiocytoma, brain stem glioma, brain tumor, cerebral astrocytoma/malignant glioma, cervical cancer, childhood cancers, colorectal cancer, esophageal cancer, Ewing's family of tumors, extracranial germ cell tumor, eye cancer, intraocular melanoma, gallbladder cancer, gastric (stomach) cancer, gastrointestinal stromal tumor (GIST), germ cell tumor, extragonadal germ cell tumor, ovarian gestational trophoblastic tumor, head and neck cancer, hepatocellular (liver) cancer, islet cell carcinoma (endocrine pancreas), Kaposi's sarcoma, kidney (renal cell) cancer, kidney cancer, laryngeal cancer, lip and oral cavity cancer, non-small cell lung cancer, small cell lung cancer, malignant fibrous histiocytoma of bone/osteosarcoma, merkel cell carcinoma, mesothelioma, nasal cavity and paranasal sinus cancer, nasopharyngeal cancer, neuroblastoma, oropharyngeal cancer, ovarian epithelial cancer, ovarian germ cell tumor, ovarian low malignant potential tumor, pancreatic cancer, paranasal sinus and nasal cavity cancer, parathyroid cancer, penile cancer, pheochromocytoma pineoblastoma and supratentorial primitive neuroectodermal tumors, pituitary tumor, pleuropulmonary blastoma, pregnancy and breast cancer, pregnancy and hodgkin's lymphoma, primary central nervous system lymphoma, rectal cancer, retinoblastoma rhabdomyosarcoma, salivary gland cancer, skin cancer (non-melanoma), skin carcinoma, merkel cell, small intestine cancer, testicular cancer, throat cancer, thymoma and thymic carcinoma, thyroid cancer, urethral cancer, uterine cancer, endometrial uterine sarcoma, vaginal cancer visual pathway and hypothalamic glioma, and Wilms' tumor.

The invention claimed is:

1. A method for treating a solid tumor comprising, locally administrating a proteinase solution, comprising proteinase K, to an extracellular space of tumor cells within the solid tumor, wherein the proteinase K, without entering into the tumor cells, kills the tumor cells by cleaving extracellular matrix proteins (ECMP) and/or the extracellular parts of transmembrane proteins (EPTMP) on a surface of the tumor cells while keeping cell membranes of the tumor cells intact before the tumor cells undergo arrest, necrosis or apoptosis.

2. The method of claim 1, wherein the proteinase solution cleaves the ECMP and/or EPTMP at the C-terminus.

3. The method of claim 1, wherein the proteinase solution cleaves the ECMP and/or EPTMP at the N-terminus.

4. The method of claim 1, wherein the proteinase solution cleaves the ECMP and/or EPTMP at the N-terminus and the C-terminus.

5. The method of claim 1, wherein the proteinase solution comprises proteinase K alone or proteinase K combined with one or more proteinases selected from the group consisting of: Pronase, trypsin, carboxypeptidase B, elastase, papain, plasmin, endoproteinase Glu-C, endoproteinase Asp-N, endoproteinase Lys-C, endoproteinase Arg-C, chymotrypsin, and carboxypeptidase Y.

6. The method of claim 1, wherein the tumor is implicated in a disease selected from the group consisting of: Adrenocortical carcinoma, appendix cancer, basal cell carcinoma, bile duct cancer, bladder cancer, bone cancer, osteosarcoma/malignant fibrous histiocytoma, brain stem glioma, brain tumor, breast cancer, cerebral astrocytoma/malignant glioma, cervical cancer, childhood cancers, colorectal cancer, esophageal cancer, Ewing's family of tumors, extracranial germ cell tumor, eye cancer, intraocular melanoma, gallbladder cancer, gastric (stomach) cancer, gastrointestinal stromal tumor (GIST), germ cell tumor, extragonadal germ cell tumor, ovarian gestational trophoblastic tumor, head and neck cancer, hepatocellular (liver) cancer, islet cell carcinoma (endocrine pancreas), Kaposi's sarcoma, kidney (renal cell) cancer, kidney cancer, laryngeal cancer, lip and oral cavity cancer, non-small cell lung cancer, small cell lung cancer, malignant fibrous histiocytoma of bone/osteosarcoma, melanoma, merkel cell carcinoma, mesothelioma, nasal cavity and paranasal sinus cancer, nasopharyngeal cancer, neuroblastoma, oropharyngeal cancer, ovarian epithelial cancer, ovarian germ cell tumor, ovarian low malignant potential tumor, pancreatic cancer, paranasal sinus and nasal cavity cancer, parathyroid cancer, penile cancer, pheochromocytoma pineoblastoma and supratentorial primitive neuroectodermal tumors, pituitary tumor, pleuropulmonary blastoma, pregnancy and breast cancer, pregnancy and Hodgkin's lymphoma, primary central nervous system lymphoma, prostate cancer, rectal cancer, retinoblastoma rhabdomyosarcoma, salivary gland cancer, skin cancer (non-melanoma), skin carcinoma, merkel cell, small intestine cancer, testicular cancer, throat cancer, thymoma and thymic carcinoma, thyroid cancer, urethral cancer, uterine cancer, endometrial uterine sarcoma, vaginal cancer visual pathway and hypothalamic glioma, and Wilms' tumor.

7. The method of claim 1, wherein the tumor cells treated by the proteinase solution become round in shape.

8. The method of claim 1, wherein the tumor cells treated by the proteinase solution resulted in dead spheres without programmed cell death or apoptosis.

* * * * *